(12) United States Patent
Wai et al.

(10) Patent No.: US 6,524,628 B1
(45) Date of Patent: Feb. 25, 2003

(54) PRESSURIZED WATER EXTRACTION

(75) Inventors: Chien M. Wai, Moscow, ID (US); Qingyong Lang, Moscow, ID (US)

(73) Assignee: Idaho Research Foundation, Inc., Moscow, ID (US)

(*) Notice: Subject to any disclaimer, the term of this patent is extended or adjusted under 35 U.S.C. 154(b) by 0 days.

(21) Appl. No.: 09/707,461

(22) Filed: Nov. 6, 2000

(51) Int. Cl.⁷ .................... A61K 35/78; A61K 31/34
(52) U.S. Cl. .................... 424/752; 424/766; 514/468
(58) Field of Search ................. 424/752, 766; 514/468

(56) References Cited

U.S. PATENT DOCUMENTS

| | | |
|---|---|---|
| 4,350,686 A | 9/1982 | Relyveld et al. |
| 4,357,361 A | 11/1982 | Lunder et al. |
| 4,683,140 A | 7/1987 | Kang |
| 4,702,915 A | 10/1987 | Këri et al. |
| 5,330,756 A | 7/1994 | Steuart et al. |
| 5,466,454 A | 11/1995 | Chang |
| 5,705,170 A | 1/1998 | Kong et al. |
| 5,770,085 A | 6/1998 | Wai et al. |
| 5,912,363 A | 6/1999 | Nafisi-Movaghar et al. |
| 6,030,621 A * | 2/2000 | De Long et al. |
| 6,117,431 A * | 9/2000 | Ramazanov et al. |
| 6,174,531 B1 * | 1/2001 | Zhang et al. |

FOREIGN PATENT DOCUMENTS

| | | | |
|---|---|---|---|
| CN | 1172669 | * | 2/1998 |
| CN | 1172670 | * | 2/1998 |
| CN | 1228432 | * | 9/1999 |
| JP | 2000128792 | * | 5/2000 |

OTHER PUBLICATIONS

Q. Lang and C.M. Wai, "An Extraction Method for Determination of Ginkgolides and Bilobalide in Ginkgo Leaf Extracts," 71 *Analytical Chemistry* 2929–2933, American Chemical Society (Jul. 15, 1999).

* cited by examiner

Primary Examiner—Christopher R. Tate
(74) Attorney, Agent, or Firm—Klarquist Sparkman, LLP

(57) ABSTRACT

Pressurized Water Extraction (PWE) is a method for extracting materials from plants by exposing a plant sample to a pressurized liquid aqueous composition. The exposure may be performed statically, dynamically, or both. For example, the sample may be exposed to a liquid aqueous composition at a temperature of from about 0° C. to about 100° C. and a pressure between about 25 atm and about 1000 atm, more typically from about 50 atm to about 200 atm. Plant materials are selectively isolated in the aqueous compositions by this method more effectively than prior methods. Moreover, the present methods provide facile extraction of thermally labile compounds, such as bilobalides from Gingko leaves.

68 Claims, 7 Drawing Sheets

BLOCK DIAGRAM OF A PWE SETUP a)

b)

PRESSURIZED WATER EXTRACTION

FIELD

The invention generally concerns a method for extracting materials from plants using pressurized aqueous compositions.

BACKGROUND

Herbal remedies are becoming increasingly popular for treating certain conditions. For example, in 1998 an estimated 10.8 million Americans used Ginkgo biloba extract, which supposedly increases memory and promotes blood thinning. Other examples of popular extracts and their purported effects include extracts of Echinacea for bolstering the immune system and extracts of St. John's wort for mood elevation.

Plant materials often have complex compositions that can vary with source and time of year, and therefore it is difficult to provide extracts of consistent quality to consumers. Furthermore, plant extract quality variabilities are exacerbated by the methods used to produce the extract. Consistent quality is especially important for extracts ingested by humans for medicinal purposes.

Solvent boiling is a common method used to prepare plant extracts. Water, or mixtures of water and various organic solvents, such as ethanol or acetone, are added to the plant material and boiled to extract the desired compounds. Solvent boiling is not selective, and therefore the extract obtained typically contains many compounds besides the desired ingredients. Another disadvantage of solvent boiling methods is the potential decomposition during the heating process of thermally labile, biologically active compounds.

Although some plant constituents can be synthesized, the major sources of such complex natural products are still the plants themselves. Therefore, in order to recover desired plant components in maximum amounts, more efficient and selective extraction methods are needed. In addition, environmentally responsible methods, which eliminate the need for organic solvents and thereby reduce disposal costs and the danger posed by exposure to such solvents, are desirable.

SUMMARY

The present invention addresses the objectives discussed in the Background. One embodiment of the present method for extracting materials from a plant comprises providing a plant sample, and then exposing the plant sample to a liquid aqueous composition. Exposing the plant sample to a liquid aqueous composition can be done statically, dynamically, or both. The sample is exposed to a liquid aqueous composition at a temperature of from about 0° C. to about 100° C. and a pressure between about 25 atm and about 1000 atm, more typically from about 50 atm to about 200 atm. Plant materials are selectively isolated in the aqueous compositions by this method more effectively than prior methods. Moreover, the present method provides facile extraction of thermally labile compounds, such as bilobalides from ginkgo leaves.

Mesh size can effect the extraction results. For terpene trilactones, such as ginkolides and bilobalides, the sample is pulverized and screened to a particle size of between about 20-mesh and about 80-mesh, preferably from about 42-mesh to about 60-mesh, before exposing the plant material to the liquid aqueous composition. Flow aids, such as sand, can be mixed with the sample to facilitate liquid flow through, around and about the plant material. Where the plant sample is from the genus Gingko, the method typically uses an aqueous compositions at a temperature between about 0° C. and about 100° C., more typically 0° C. and about 80° C., and preferably between about 0° C. and about 60° C.

Terpene trilactones selectively extracted from plant material by the present pressurized water extraction (PWE) method may have the following Formula I, which is representative of the ginkolides.

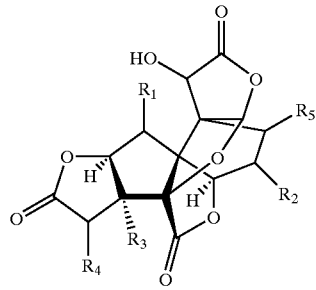

Formula I

With reference to Formula I, $R_1$ is selected from the group consisting of —H and —OH; $R_2$ is selected from the group consisting of —H and —OH; $R_3$ is selected from the group consisting of —H and —OH; $R_4$ is selected from the group consisting of —H and lower aliphatic, particularly lower alkyl, such as methyl; and $R_5$ is selected from the group consisting of —H, —OH, and lower aliphatic, particularly sterically hindered lower alkyl groups, such as isopropyl, t-butyl or neopentyl.

The terpene trilactone also may have the following Formula II, which is representative of the bilobalides.

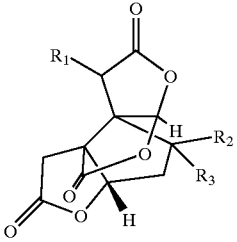

Formula II

With reference to Formula II, $R_1$ is selected from the group consisting of H and —OH; and $R_2$ and $R_3$ are independently selected from the group consisting of —H, —OH, and lower aliphatic, particularly lower alkyl such as methyl, ethyl, n-propyl, isopropyl, n-butyl, sec-butyl and t-butyl.

The PWE method allows extractions to be conducted at relatively low temperatures, e.g., below about 100° C., compared to known methods. Thus, a currently preferred method involves a room temperature method for extracting terpene trilactones from plants; particularly terpene trilactones soluble or at least partially soluble in water or aqueous based solutions. Such extractions can be quantitative. This embodiment of the present PWE method comprises providing powdered plant material having a mesh size between about 42-mesh and about 60-mesh, passing aqueous compositions through the powdered plant material at a temperature less than 100° C. and a pressure of at least about 50 atm (e.g., about 100 atm), and isolating material solubilized in such aqueous compositions.

The term aqueous composition as used herein includes, but is not limited to, pure water (e.g. distilled, doubly distilled, or deionized water), substantially pure water, and aqueous solutions containing modifiers. Substantially pure water refers to water containing dissolved or suspended materials that are not intentionally added to facilitate extraction of materials. Tap water, ground water, partially deionized water, and surface water are non-limiting examples of substantially pure water.

DETAILED DESCRIPTION

I. Abbreviations

Figure 1:
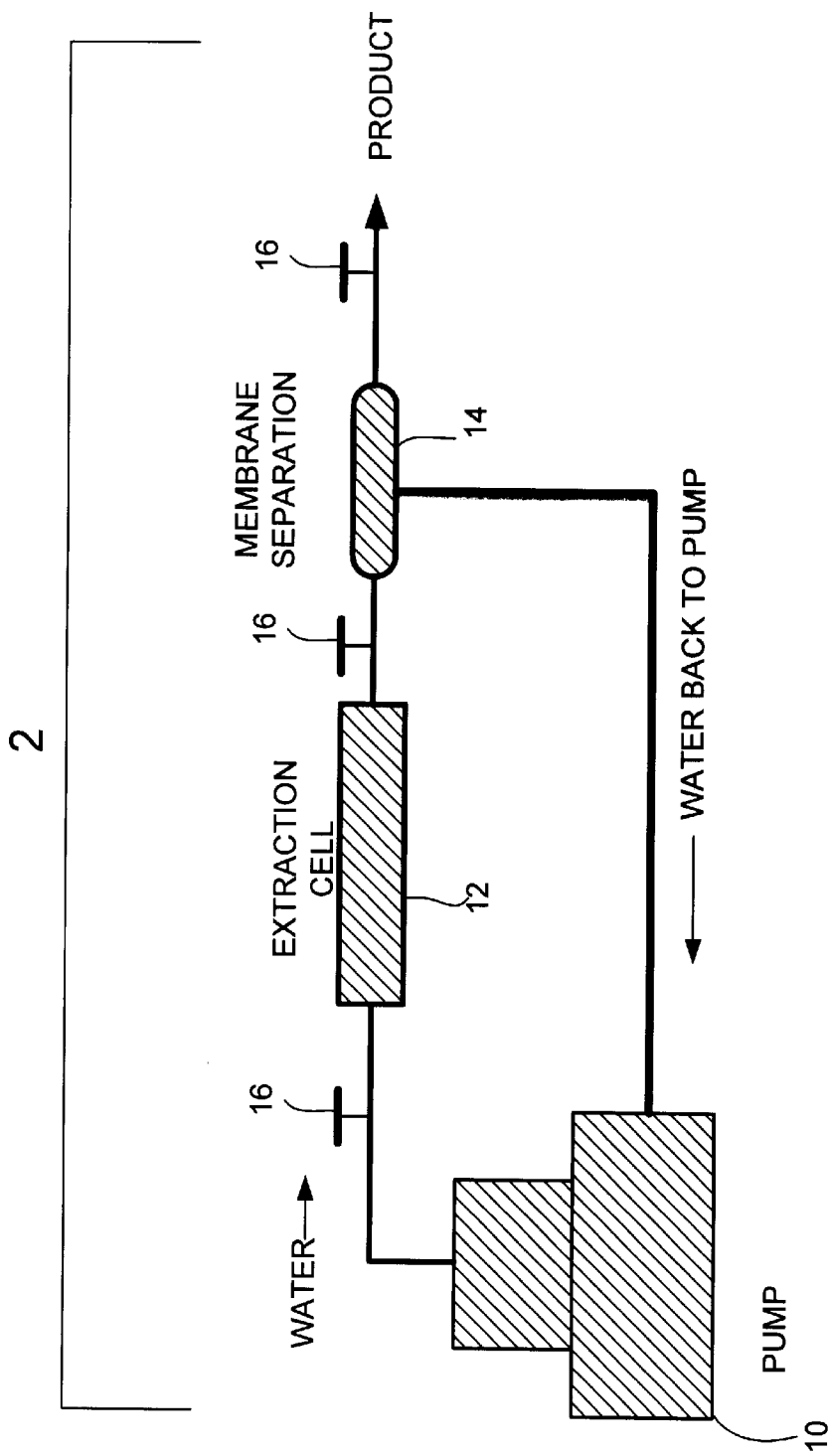
FIG. 1 is a block diagram of an apparatus useful for practicing the disclosed pressurized water extraction (PWE) methods.

PWE—pressurized water extraction
B-B—bilobalide
G-A—gingkolide A
G-B—gingkolide B
G-C—gingkolide C II. Pressurized Water Extraction Water has several properties that make it an ideal solvent for obtaining plant extracts from plant materials. First, water is the safest, cheapest and most available solvent. Second, the pH of water may be adjusted to increase or decrease the solubility of acidic and basic compounds. Finally, the solvent properties of water vary with temperature. As the temperature of water is increased, particularly under pressure, it becomes capable of dissolving a greater variety of compounds.

Extracting materials from plants using water typically requires elevated temperatures. At low temperatures water is unable to penetrate plant parts and solubilize plant constituents. However, increasing the temperature may be undesirable because oxidation and rearrangement reactions are accelerated and thermally labile compounds may be lost. Therefore, using water to extract thermally labile natural products requires a different approach.

The pressurized water extraction (PWE) method of the present invention is useful for preparing extracts from plant materials, especially herbal plant materials. PWE relies in part on the apparent ability of water molecules under pressure to penetrate into plant materials. Pressures of generally greater than about 25, typically greater than about 50 atm and up to about 1000 atm are useful. The penetration of water molecules into plant materials under such pressures allows rapid extraction of plant components at temperatures lower than the boiling point of water, e.g., at room temperature which is a particularly beneficial feature of the present invention. PWE provides an advantage over low temperature/low pressure boiling solvent extraction methods in that volatile compounds are not removed from the extraction solvent during the process.

PWE at low temperatures, such as below about 100° C. also provides increased selectivity over solvent boiling methods. More specifically, low temperature PWE selectively extracts polar and moderately polar compounds, such as the terpene trilactones, leaving behind significant amounts of non-polar compounds. This extraction selectivity results in a less complicated, higher quality extract.

The pressures employed with PWE also allow higher temperatures to be employed. Any temperature up to the critical temperature of water (374.2° C.) may be employed if sufficient pressure ($P_c$ for water equals 218 atm) is applied to maintain the water in its liquid state. For example, at a pressure of 100 atm, it is possible to heat water to about 301° C. and still maintain a liquid state according to the Clausius-Clapeyron Equation. While high temperatures may not be desirable in some applications, for example because selectivity is reduced, high temperatures may be useful in other applications. For example, high temperatures, such as temperatures greater than 100° to about 300° C., may be useful for extracting non-cellulosic materials from plants to recover cellulose.

III. Plant Material

The materials preferably extracted by the present PWE method are naturally occurring, plant-derived materials such as roots, leaves, stems, fruits, and seeds. Without limitation, terpenoids, such as ginkolides and bilobalides, and flavonoids, such as catechins, catechin derivatives, and catechin oligomers, and phenolic compounds, such as gallic acid, are examples of materials that can be selectively extracted from plant materials, particularly leaves and seeds, by the method of the present invention. Chemical structures for Ginkolides A-C (Formula III) and Bilobalide (Formula IV) are provided below.

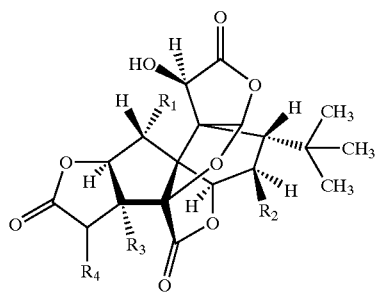

Formula III

With reference to Formula I, Ginkgolide A has $R_1=R_2=H$, and $R_3=OH$; Ginkgolide B has $R_1=R_3=OH$, and $R_2$=H; Ginkgolide C has $R_1$=$R_2$=$R_3$=OH and compound J has $R_1$=H, $R_2$=$R_3$=OH.

Formula IV

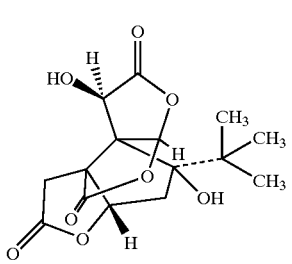

Based on Formulas III and IV, the present PWE method is particularly selective for extracting terpenoids, particularly terpene trilactones, from plant materials. Examples of such terpene trilactones may have general Formula I (ginkolides) and Formula II (Bilobalide) below.

Formula I

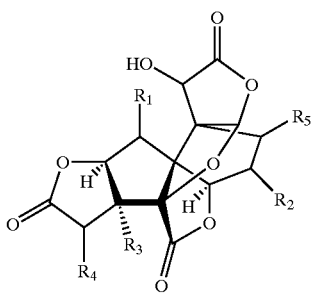

Stereochemistry is specifically not depicted on general Formulas I and II because the extraction technique extracts all possible stereoisomers of a particular class of compounds. With reference to Formula I, $R_1$ is selected from the group consisting of —H and —OH; $R_2$ is selected from the group consisting of —H and —OH; $R_3$ is selected from the group consisting of —H and —OH; $R_4$ is selected from the group consisting of —H and lower aliphatic, particularly lower alkyl, such as methyl, where "lower" means chains, both straight and branched, having 10 or fewer carbon atoms, including all position and stereoisomers of such compounds; $R_5$ is selected from the group consisting of —H, —OH, and lower aliphatic, particularly lower alkyl, and even more particularly sterically hindered lower alkyl groups, such as isopropyl, sec-butyl, t-butyl, and neopentyl groups.

Formula II

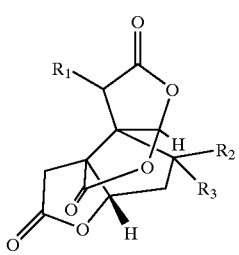

With reference to general Formula II, $R_1$ is selected from the group consisting of —H and —OH; and $R_2$ and $R_3$ are independently selected from the group consisting of —H, —OH, and lower aliphatic, particularly lower alkyl, and even more particularly sterically hindered lower alkyl groups, such as isopropyl, sec-butyl, t-butyl, and neopentyl groups.

Examples of flavonoids and phenolic compounds include compounds with the structures given below in Formulas V, VI, VII and VIII.

Formula V

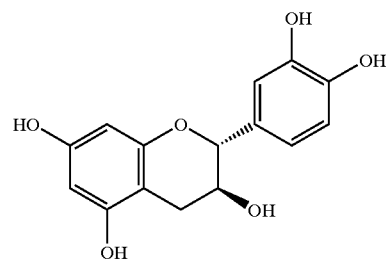

Catechin

Formula VI

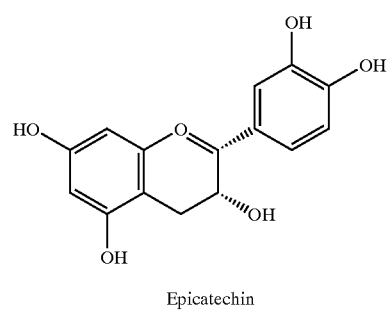

Epicatechin

Formula VII

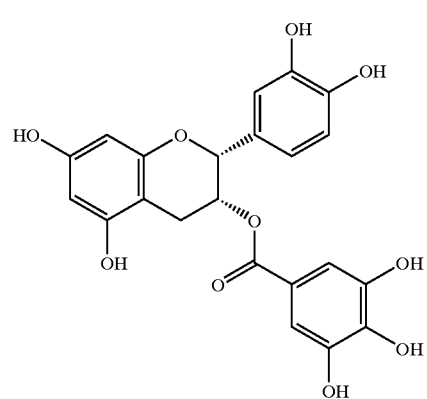

Epicatechin Gallate

Formula VIII

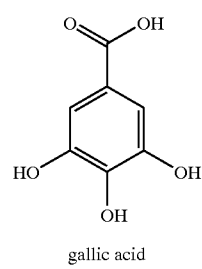

gallic acid

IV. Apparatus for Pressurized Water Extraction

Figure 2:
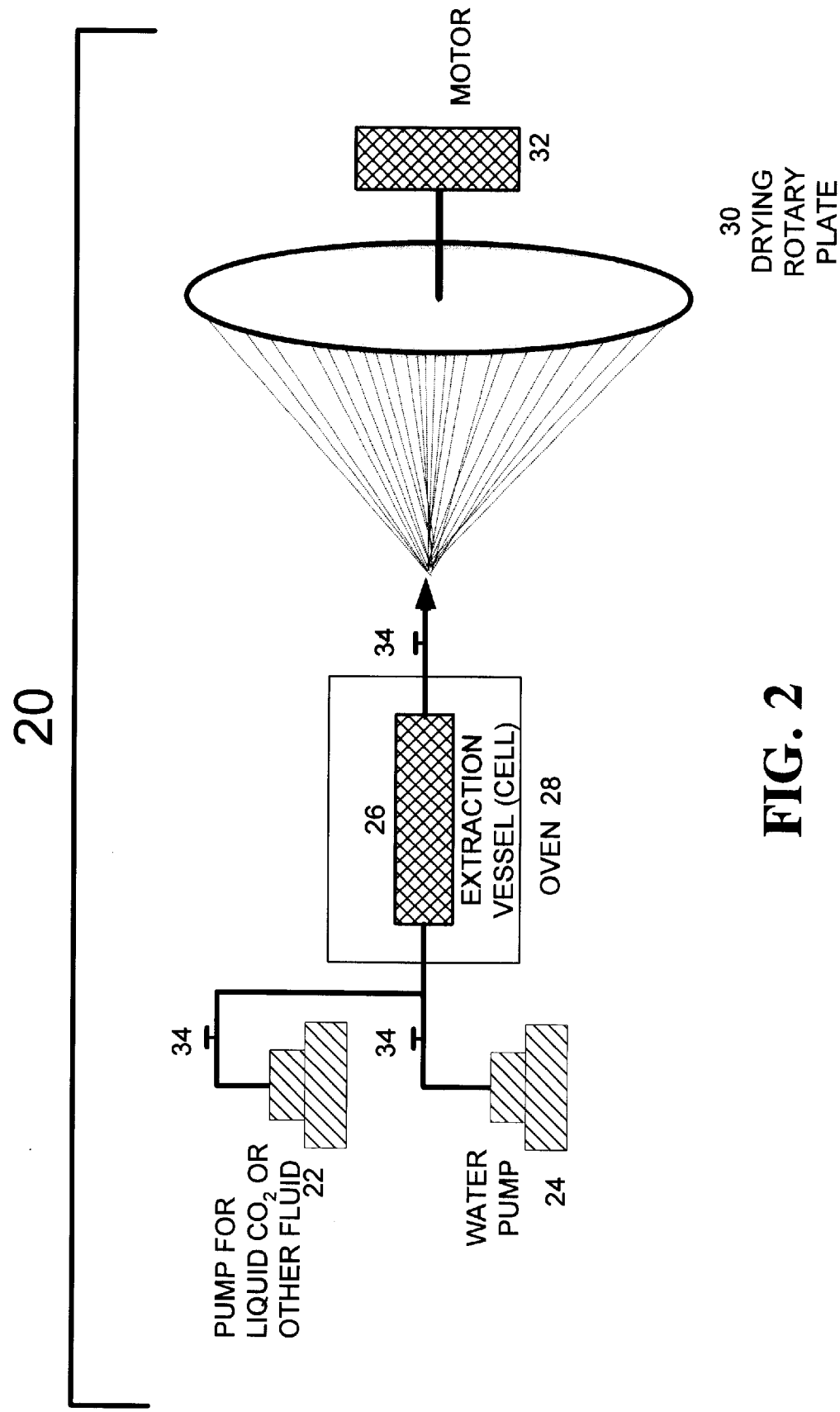
FIG. 2 is a block diagram of another embodiment of an apparatus useful for practicing the disclosed PWE methods.

The PWE method may include static extraction under pressure, a dynamic extraction, where the pressurized aqueous composition is forced through a sample of plant material, or both. Two systems suitable for practicing PWE are illustrated in FIG. 1 and FIG. 2. High pressure extraction devices also are described in the inventors' prior U.S. patents, and patent applications, directed to supercritical fluid extractions, such as U.S. Pat. Nos. 5,356,538, 5,730,874, 5,770,085, 5,840,193, 5,840,193, 5,965,025, U.S. patent application Ser. No. 09/137,563, entitled Method And Apparatus For Dissociating Metals From Metal Compounds Extracted Into Supercritical Fluids, and U.S. patent application Ser. No. 09/306,948, entitled Method For Separating Metal Chelates From Other Materials Based On Solubilities In Supercritical Fluids. Each of these patents and applications is incorporated herein by reference.

The extraction apparatus may be scaled suitably for analytical extractions of plant materials or larger for commercial scale preparation of plant extracts. Extraction system 2 of FIG. 1 includes a pump 10, and an extraction cell 12. Optionally, system 2 may include a membrane separation device 14 to remove extracted materials from the pressurized aqueous composition after it has passed through the extraction cell 12. The apparatus also may include a flow regulators 16 for establishing a return flow of an aqueous composition that allows the aqueous composition (with or without removal of extracted materials) to be circulated continuously through the extraction cell 12. A suitable laboratory embodiment of a PWE apparatus may use as a pump 10 an ISCO (Lincoln, Nebr.) Syringe Pump Model D with a capacity of 266 mL, pressure range of 0.7 to 510.2 atm, and a flow rate range of 0.001 mL/min to 107 mL/min. The extraction cell 12 may be constructed or purchased for example from Keystone Scientific Inc., Bellefonte, Pa. and, in a laboratory scale embodiment, may have a volume capacity of about 0.5 mL to about 1.5 L. A suitable laboratory scale membrane separation device 14 may be constructed or purchased from Biolab Equipment Canada Ltd. and fitted, for example, with a DK 2521T, Desal 5 thin film membrane also available from Biolab Equipment Canada Ltd (Oakville, Ontario, Canada).

Extraction system 20 of FIG. 2 includes two pumps 22 and 24 that provide pressurized liquid carbon dioxide and pressurized aqueous compositions, respectively. The apparatus also includes an extraction vessel (cell) 26 inside of oven 28, and a rotary drying plate 30 driven by motor 32. The apparatus also includes flow regulators 34 for establishing flows of liquid carbon dioxide and aqueous compositions through extraction vessel 26. In this embodiment, pressurized liquid carbon dioxide may be mixed with aqueous compositions to provide an extraction solvent mixture before entering the extraction vessel 26. The mixture of liquid carbon dioxide is then allowed to vaporize (for example, by lowering the pressure) upon leaving the extraction vessel 26. The mechanical energy resulting from the vaporization of the liquid carbon dioxide atomizes the extraction solution allowing for rapid evaporation of the water component of the extraction solvent, leaving the extracted compounds as solids which are deposited on rotary drying plate 30. Rotary drying plate 30 may be continually spun by motor 32 during the extraction process.

EXAMPLES

The following examples are provided to illustrate certain features of working embodiments of the present invention. The scope of the invention should not be limited to those features exemplified by such examples.

Example 1

PWE Extraction of Gingko Biloba

In this example PWE was used to extract, at low temperature, the active ingredients from samples of plants of the genus Gingko. PWE also was compared to several commonly used boiling methods. Gingkolides and Bilobalide were selectively separated with a liquid-liquid extraction and then readily quantified with a fast GC-FID method. (Lang and Wai, *Anal. Chem.*, 71:2929–2933, 1999)

Of all the methods tested, PWE provided the best results in terms of efficiency and, especially, selectivity. For example, the PWE extraction method is particularly useful for recovering Bilobalide, the least stable of the four known active terpene trilactones in ginkgo leaves. Significant losses of Bilobalide were observed in the solvent boiling processes and in high temperature PWE.

Sample Collection and Preparation

Ginkgo leaves were collected from three different trees (two young ginkgo trees and one old tree) on the University of Idaho campus at different times of 1997. Two other green ginkgo leaf samples also were analyzed, one of which was collected from California in May of 1997 and the other from Taixing, China, in August of 1997.

All the leaf samples were air dried at room temperature in a clean laboratory hood, pulverized separately in a coffee grinder and passed through sieves to obtain desired particle sizes. The powder samples were kept in clean glass bottles and stored in a refrigerator at $\leq 4°$ C.

Chemicals and Instrumentation

Gingkolides A, B and Bilobalide (HPLC grade) were purchased from Sigma. Other reagents included bis (trimethylsilyl) acetamide (BSA) (derivatization grade, Aldrich); ethanol (200 proof, McCormick Distilling Co.); acetone (certified A.C.S., Fisher); methanol (HPLC grade, Fisher); methylene chloride (HPLC-GC/MS grade, Fisher); ethyl acetate (certified A.C.S., Fisher), fine sand (80-mesh, lab prepared); tetrahydrofuran (THF) (Certified A.C.S., Fisher); acetic acid (Certified, A. C. S., Fisher), $NaH_2PO4.H2O$ (J. T. Baker Chemical Co.), squalane (99%, Aldrich) and nitrogen (99.999%, Oxarc).

All standard solutions of gingkolides and Bilobalide were prepared as received. The whole packages were dissolved in methanol, and volumes were adjusted so that the final concentrations to 100 $\mu$g/mL (100 ppm). These stock solutions were kept in a freezer, and were stable for at least several weeks.

A Hewlett Packard 5890 gas chromatography installed with a DB-5 column (30 m×0.32 mm×0.25 $\mu$m) was used for quantitative analyses. A flame ionization detector (FID) was used for the detection.

An ISCO supercritical fluid extractor, SFX™ 2–10, equipped with an ISCO syringe pump, model 260 D, and a series D pump controller were used for the PWE.

Extraction of Gingkolides and Bilobalide

PWE: A 10 mL sample cell was packed first with 2 g of fine sand at bottom, then 1 g of powder leaf sample mixed with 1 g of sand at middle, and finally 1 g of sand on top. Room temperature water containing 0.5 % acetic acid was used as the aqueous composition. For most experiments, an aqueous composition at 100 atm of pressure was first mixed with the leaf sample for a 15-minute period of static extraction. Then, with the outlet valve slowly opened, dynamic extraction was started. The flow rate was typically controlled between 1.5 to 2.0 mL/min. The extraction was stopped when 20 mL of extract had been collected. The sample solution was adjusted to pH$\approx$5 with dilute NaOH, and the final volume was made to 25 mL in a volumetric flask. One mL of this solution contained the extract from 40 mg of Ginkgo leaves.

Solvent Boiling Methods: Five different solvents including ethanol, methanol, acetone, water, and a mixture solvent of methanol (30%) and water (70%) were used for the extractions, and all the results were based on duplicate extractions. In 20 mL of each solvent, 1 g aliquots of a Ginkgo leaf sample were boiled gently on a hot plate for two times, the first time for 2 to 3 minutes and the second time for 15 to 20 minutes. The solid residue was removed by filtration using a No. 4 Whitman filter paper. The final volume of all samples was adjusted to 50 mL. One mL of this solution corresponded to the extract from 20 mg of leaves.

For samples prepared with water solutions, whether PWE or in solvent boiling methods, 5 mL of the solution were directly used for the following separation and analysis. For samples prepared with organic solvents or mixed solvents, 5 mL of solution from each of the samples were transferred into a beaker, and evaporated on a hot plate to near dryness to remove the organic solvents. The solid sample residue was dissolved in 5 mL of warm water that was adjusted to pH≈5 prior to use. Ultrasonic agitation was used to complete the dissolution, if necessary.

Separation of Gingkolides and Bilobalide

Exactly 5 mL of the aqueous solution containing the extracted compounds were transferred into a 50 mL separatory funnel, and extracted three times with 5 mL of a mixture of methylene chloride and ethyl acetate (v/v 3:2), each time by gently shaking for about 1 minute. The organic phases were combined and dried over a small amount of anhydrous $Na_2SO_4$. The final volume was adjusted with ethyl acetate to 15 mL in a volumetric flask.

Occasionally, an emulsion phase formed during the extraction. Adding a small amount, such as about 1 mL, THF to the emulsion effectively increased the phase separation rate. A small amount of THF did not affect the extraction results.

Determination of Gingkolides and Bilobalide

After the liquid-liquid extractions, exactly 5 mL of each of the organic solutions were transferred into separate sample vials, and the solvent was removed by evaporating to dryness using a gentle stream of nitrogen gas in a hood. Each sample vial was spiked with 200 μl of BSA [bis (trimethylsilyl) acetamide]. The vials were then tightly capped, and placed into a GC oven at 100° C. for one hour for derivatization. After derivatization, 50 μg/g of squalane was spiked into each sample as an internal standard (IS) and the final volume was made to 1.0 mL with methylene chloride. Depending on the concentration of gingkolides and Bilobalide, 1 or 2 μl of the solution was injected onto a GC for quantification.

Nitrogen was used as the carrier gas. Column head pressure was set at 18 psi, which corresponded to a column flow rate of approximately 3.0 mL/min. The injector was set at 280° C. and the detector at 300° C. The GC temperature program was started from the initial temperature of 200° C., held there for one minute, and increased to 280° C. at the rate of 10° C./min, where it was held for 6 minutes. For each sample, the total GC analysis time was 15 minutes.

The concentrations of gingkolides and Bilobalide in the samples were calculated based on the peak areas of the analytes and the IS. Since no commercial standard Gingkolide C was available, its identification was made by its mass spectrum, and its concentration was based on the FID responding ratio for gingkolide B. Because the FID responding ratios for Gingkolides A and B were almost the same, this approximation appears reasonable.

A series of standard solutions (10 to 200 ppm of each of the compounds with 50 μg/g of squalane) were prepared and derivatized simultaneously with the leaf samples. Over this concentration range, the FID responding ratio for the analytes and the IS was stable.

Factors Affecting PWE Results

In order to achieve maximum extraction, factors that might affect the extraction results were investigated. Factors that were investigated included the extraction temperature, pressure, pH of the aqueous composition, flow rate and sample particle sizes. Temperature and pH have the most significant influences on the extraction results for Gingko.

Temperature: The pressure was set at 100 atm, and flow rate set between 1 to 2 mL/min. Following 15 minutes of static extraction, a dynamic extraction was started. After 20 mL of extract were collected, the extraction was stopped. The pH of the aqueous composition used for the extraction was adjusted with acetic acid to pH≈5.

Figure 3:
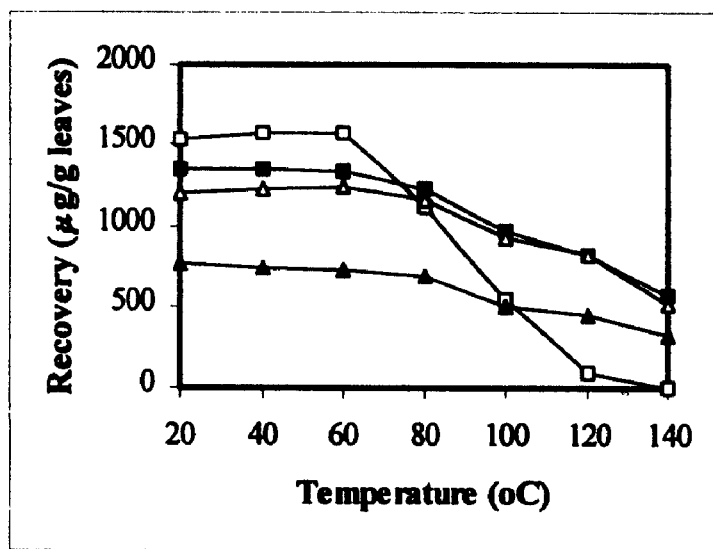
FIG. 3a is a graph of temperature (°C.) versus amount of material recovered (μg/g leaves extracted) that shows (a) temperature effects on the extraction results of bilobalide [B-B (□)], gingkolide A [G-A (■)], gingkolide B [G-B (▲)] and gingkolide C [G-C (Δ)].
FIG. 3b provides chromatograms of a leaf sample extracted at 140° C. (top) and room temperature (bottom), with the peak markings being (1) B-B, (2) IS (internal standard, squalane); and (3–5) Ginkgolides A-C, respectively.
Figure 3:
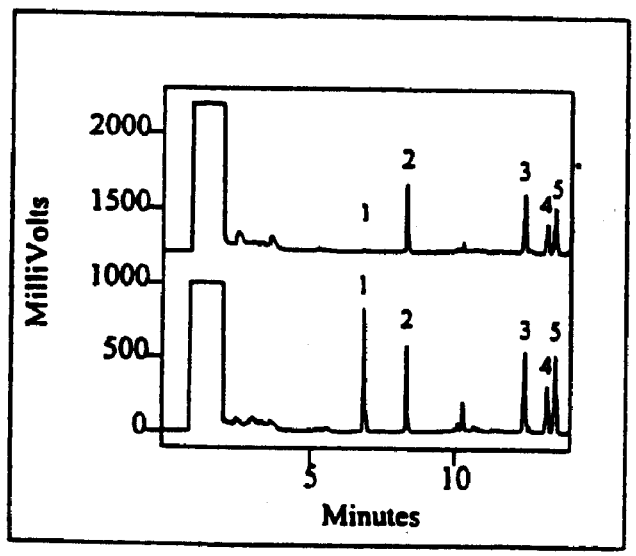

FIG. 3(a) plots PWE results versus extraction temperatures. When the temperature was raised from room temperature, i.e., about 20° C. to 60° C., only small changes in recovery of the terpene trilactones were observed. Above 60° C., terpene trilactones recoveries started to decrease. Compared with the extraction results at room temperature, about one fourth of the bilobalide was lost at 80° C., about two thirds was lost at 100° C., and all was apparently lost at 140° C. (See FIG. 3(b)). For the gingkolides, compared with their recoveries at ≦60° C., at least one fourth was lost at 100° C. and only about half was as extracted at 140° C.

Above 100° C. significant quantities of additional compounds also were extracted. At 140° C., so many compounds were extracted that the extract solutions became thick and almost black. Increased amounts of organic material in the extracts at higher temperatures may present clogging problems, make chemical analysis difficult, and lower the quality of the extract.

Based on the above observations, low temperature extractions are preferred. As used herein, "low temperature" means generally a temperature lower than 140° C., preferably lower than 100° C., even more preferably less than 80° C., with best selective extraction results being achieved with a temperature lower than about 60° C. Thus, room temperature PWE extractions, such as from about 10° C. to about 30° C., can be used for selective extraction, particularly for the terpene lactones, such as the terpene trilactones. PWE at room temperature not only enabled the maximum recoveries of terpene trilactones and provided high selectivity with respect to extracting such materials from plant materials, it also is the most economical extraction method because no heat energy is required.

Figure 4:
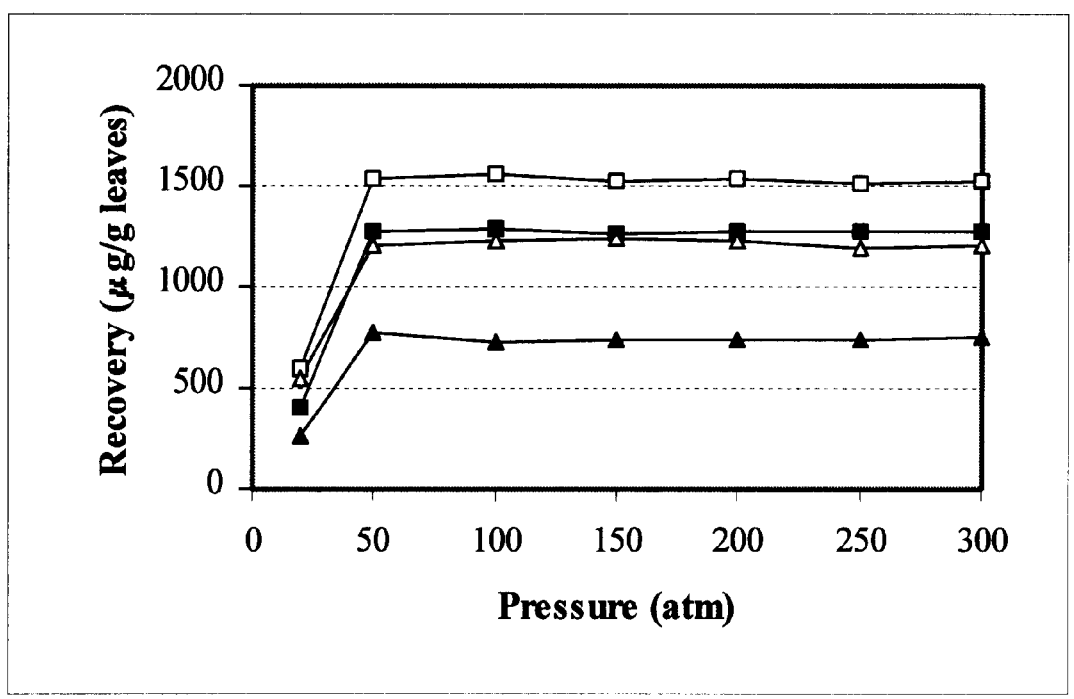
FIG. 4 is a graph of pressure (atm) versus recovery of material (μg/g leaves extracted) which illustrates the effect of pressure on the extraction results of B-B (□), G-A (■), G-B (▲) and G-C (Δ) at room temperature with a flow rate of 1–2 mL/minute and an extraction volume of about 20 mL.

Pressure: A "threshold" pressure was observed for the extractions of terpene trilactones from the leaf samples. Below the threshold pressure, either the solvent could not flow through the sample bed due either to the (1) low porosity of the packed leaf powders or (2) slow diffusion of the solvent through the sample matrices. For Gingko samples, the threshold pressure was approximately 50 atm (see FIG. 4).

In this instance, increasing the pressure above this threshold pressure had little effect on the extraction results. A barrier layer may be formed by the leaf surface wax, a hydrophobic material on the leaves that protects them from losing moisture under natural conditions. The threshold pressure may coincide with that pressure required to allow the solvent molecules to penetrate the surface barrier and into the leaf particles.

In the experiments hereafter, 100 atm pressure was used for all the extractions. Pressures lower than about 200 atm, and preferably pressures from about 50 atm to about 100 atm, are preferred because extraction equipment that operates at these pressures is less expensive and more reliable. In general, pressure in the range from about 25 atm to about 1000 atm are useful, with pressures in the range from about 50 atm to about 200 atm providing the best extraction results. Some plant materials, having greater amounts of wax, may however exhibit a higher threshold pressure and thus require a pressure greater than 100 atm, and up to about 1000 atm.

pH: Aqueous buffer solutions having a pH from 2 to 9 were prepared and used to perform PWE at room temperature and 100 atm pressure. Acids or salts used for these experiments included mineral acids, such as hydrochloric acid (HCl), lower alkyl organic acids, such as formic acid (CHOOH) and acetic acid ($CH_3COOH$), citric acid, $H_3PO_4$, sodium acetate, sodium citrate, $NaH_2PO_4$, $Na_2HPO_4$ and $Na_2CO_3$. The best extraction result for Gingko, in terms of efficiency and selectivity, were obtained using dilute (v/v 0.5%) phosphoric acid or acetic acid. Because acetic acid is ingestible it is safer and more acceptable for herbal extracts.

Figure 5:
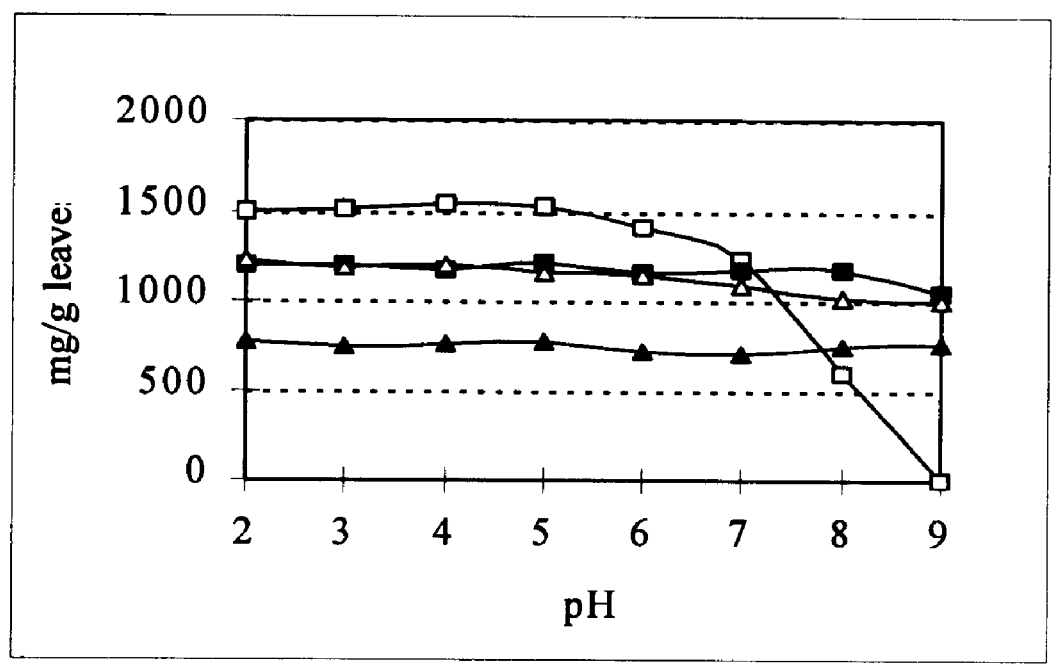
FIG. 5 is a graph of pH versus amount of material recovered (mg/g leaves extracted) which illustrates the effect of pH on the extraction results of B-B (□), G-A (■), G-B (▲) and G-C (Δ).

Although the solubility of Gingkolides should be increased under basic pH conditions because they could undergo reversible ionization reactions, the recovery of Bilobalide actually decreased with increasing pH (FIG. 5). At pH 8, more than half of the Bilobalide was lost, while at pH $\geq 9$ no detectable Bilobalide was left. The pH effects on Bilobalide extraction may be due to irreversible hydrolysis and lactonization reactions. Therefore, weakly acidic conditions are preferred for Bilobalide extractions.

In this instance, high pH ($\geq 8$) also led to co-extraction of large amounts of additional compounds. As mentioned above, large quantities of additional compounds deteriorate the quality of the extract and also cause difficulties in extraction analysis.

Particle Size: Sample particle size can affect the diffusion rates of both the solvent and the dissolved solutes from the sample particles by altering the porosity of the sample bed in the extraction cell. Four particle size ranges were examined for Ginkgo samples, including 20<d>42, 42<d>60, 60<d>80 and d<80 mesh.

Figure 6:
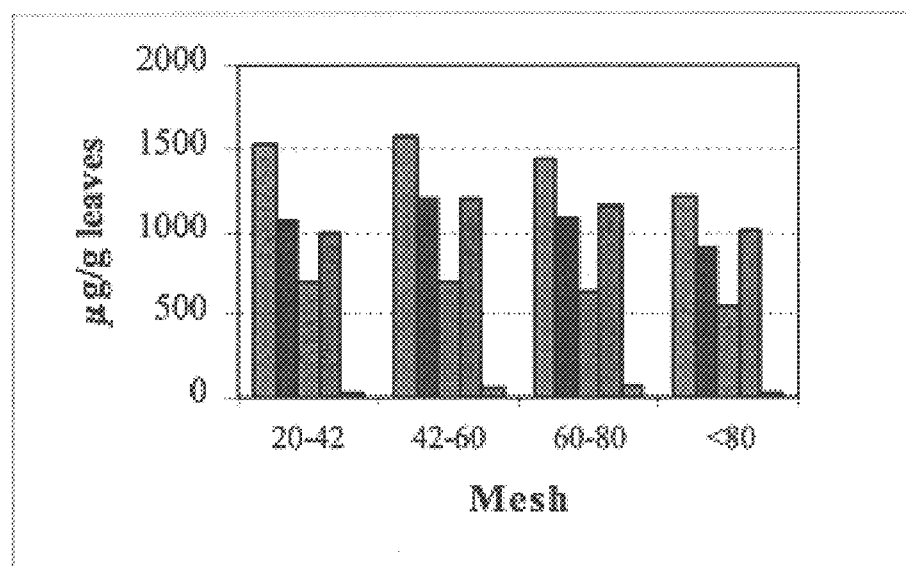
FIG. 6 is a graph of screen mesh size versus amount of material recovered (μg/g leaves extracted) which illustrates the effect of sample particle size on the extraction results of (columns from left to right) Bilobalide and Gingkolides A, B, C and compound J, respectively.

As the extractions were performed under identical conditions, the extraction results versus the particle sizes are shown as a histogram in FIG. 6. Instead of the finest particles (<80-mesh), 42–60-mesh particles were found to be the best size range for maximum extractions from Gingko. Further tests indicated that particles passing through a 42-mesh sieve provided equally good extractions.

Samples with particle sizes in the range of 20–42 mesh required prolonged extractions. This was probably because more time was needed for the dissolved solutes to diffuse out of the sample particles. Consequently, a lower extraction rate resulted. On the other hand, if the particle sizes were too small, e.g., $\leq 80$-mesh, the porosity or the permeability of the sample bed was reduced so that, in a limited extraction time or volume, not all the sample particles could effectively act with the solvent molecules.

From the particle size tests it is apparent that in order to achieve maximum extractions of raw herbal materials they should be pulverized into a suitable size range. Too coarse or too fine powder may result in lower efficiencies. For Ginkgo leaves, 42-mesh is a suitable upper limit for PWE. The optimal particle size for other plant materials may be larger or smaller.

Modifiers: Modifiers include, but are not limited to, acids (e.g., acetic acid), bases, salts (e.g., $KH_2PO_4$), buffers (e.g., phosphate buffers and acetate buffers), antimicrobials (e.g. antifungals), organic modifiers (e.g, water miscible solvents including methanol, ethanol, and acetone) and combinations thereof. Modifiers may serve to adjust the pH of the aqueous composition (e.g., between pH=0 and pH=14), alter the ionic strength of the aqueous compositions (e.g., between about 0 and 4 molar, for example, 10% NaCl, which is approximately 2 M in NaCl, is effective at increasing selectivity), adjust the solvating power (polarity) of the aqueous composition (e.g., adjust the polarity index of the solution from about 4 to about 10.2), or to prevent microbial growth, for example, growth of mold, in the aqueous composition. Useful acids or salts include, but are not limited to, mineral acids, such as hydrochloric acid (HCl) and nitric acid ($HNO_3$), lower alkyl organic acids, such as formic acid (CHOOH) and acetic acid ($CH_3COOH$), citric acid, phosphoric acid ($H_3PO_4$), sodium acetate, mono-, di-, and tri-basic sodium citrate, potassium acetate, mono-, di-, and tri-basic potassium citrate, $NaH_2PO_4$, $Na_2HPO_4$, $Na_2CO_3$, $KH_2PO_4$, $K_2HPO_4$, and $K_2CO_3$.

Modifiers may be present in amounts ranging from about 0.001 percent to about 50 percent, such as from about 0.001 percent to about 10 percent, for example from about 0.001 percent to about 5 percent.

Modifiers may be present in amounts that adjust the properties of an aqueous composition to facilitate extraction of certain materials from particular plant materials. For example, the pH of an aqueous composition may be adjusted by adding acids, bases, or buffers to promote ionization of acidic and/or basic groups on desired materials, thereby increasing their solubility in the aqueous composition. The pH may similarly be adjusted to decrease the solubility of undesirable materials. The pH may also be adjusted to prevent undesirable reactions that destroy desirable materials. In some embodiments, the ionic strength of the aqueous composition may be increased to lower the solubility of undesirable materials in the aqueous composition or to enhance the penetration of the aqueous composition into plant materials. The ionic strength may be adjusted to depress the dissociation or ionization of the desired compounds in herbal materials. For example, ginkgolides, particularly bilobalide, can undergo irreversible ionization reactions. With the addition of some salt(s), such as NaCl, this ionization can be controlled.

Other Factors: In order to keep a stable flow rate, it was found helpful to mix the leaf powder with a certain amount of a finely divided flow aid, such as fine sand. In the case of Gingko, the proper sample-to-sand ratio was about 1:1, and fine sand (e.g., about 80-mesh or smaller) worked better than regular sea sand. Coarse sand was less effective, probably due to flow-through channels in the sample.

Before dynamic extraction, a static extraction may be used to lower the extraction volume to a reasonable volume, e.g., 20 mL of extract. Ten minutes of static extraction were found sufficient for quantitative extraction of terpene trilactones, such as gingkolides and Bilobalide, in a total volume of 20 mL. However, static extraction for more than 15 minutes did not result in any further improved extractions. Flow rate did not affect the extraction results in this example as long as it was controlled below 3 mL/minute. A flow rate of 1.5 to 2 mL/minute was found best for the analytical scale extractions performed in this instance. For commercial-scale extraction, up to 1000 liter or larger vessels suitable for PWE (e.g. those used in commercial scale extraction of caffeine from coffee using SFE) are available or may be constructed by those of ordinary skill in the art. Flow rates may be greater than 10 gallon/minute in commercial scale embodiments.

In summary, quantitative extraction of gingkolides and bilobalide at room temperature and 100 atm pressure from leaf samples with ≦42-mesh particle size was achieved using 20 mL of an aqueous composition containing 0.5% of acetic acid. The extraction results for all the terpene trilactones are reproducible.

Comparison of Extraction Methods

Table 1 presents extraction results for Ginkgo leaf samples using solvent boiling methods PWE, and supercritical fluid extraction (SFE). No boiling method matched the extraction results obtained with the PWE method. Reasons for the lower extraction efficiencies of the boiling methods may include thermal decomposition or other undesired reactions during the extraction process. In addition to lower efficiency and selectivity, the solvent boiling methods require more time and energy input.

TABLE 1

Comparison of PWE and Solvent Boiling Extraction Methods

| Method[a] | B-B (µg/g leaves) | G-A (µg/g leaves) | G-B (µg/g leaves) | G-C (µg/g leaves) | Total (µg/g leaves) | Recov. (%)[b] |
|---|---|---|---|---|---|---|
| Acetone | 915 | 864 | 361 | 514 | 2654 | 54 |
| Ethanol | 1358 | 1326 | 625 | 771 | 4080 | 83 |
| Methanol | 1192 | 1204 | 617 | 769 | 3692 | 77 |
| Water | 1343 | 1344 | 629 | 745 | 4061 | 83 |
| Methanol/water | 859 | 926 | 482 | 686 | 2953 | 60 |
| PWE | 1582 | 1360 | 771 | 1197 | 4910 | 100 |
| SFE | — | 1318 | 727 | 1038 | 3065 | — |

[a]Solvent boiling methods and PWE.
[b]Relative % to those of PWE.

The SFE method using supercritical carbon dioxide as the extraction solvent is more effective than PWE in removing flavonoid compounds from Gingko (as judged by the color solid residue obtained after SFE) and, at elevated temperature, is equally effective as the PWE method for extracting terpene trilactones. However, its selectivity for terpene trilactones is lower than the PWE method. Bilobalide was not analyzed in the SFE method.

PWE is a closed system so when pressure is applied, the solvent or the acid molecules can effectively penetrate through the surfaces of the leaf particles to replace and then remove the targeted molecules from the matrix sites. During the entire extraction process, the aqueous composition is continuously forced through the sample bed so that maximum dissolution and removal of the terpenoids are possible. At room temperature, many undesired reactions, such as decomposition or degradation reactions, do not take place. Most of the impurity compounds, especially lipophilic compounds, are not dissolved in the aqueous composition; therefore, the selectivity is higher for the moderately polar terpene trilactones.

Kinetic Extraction Studies

Figure 7:
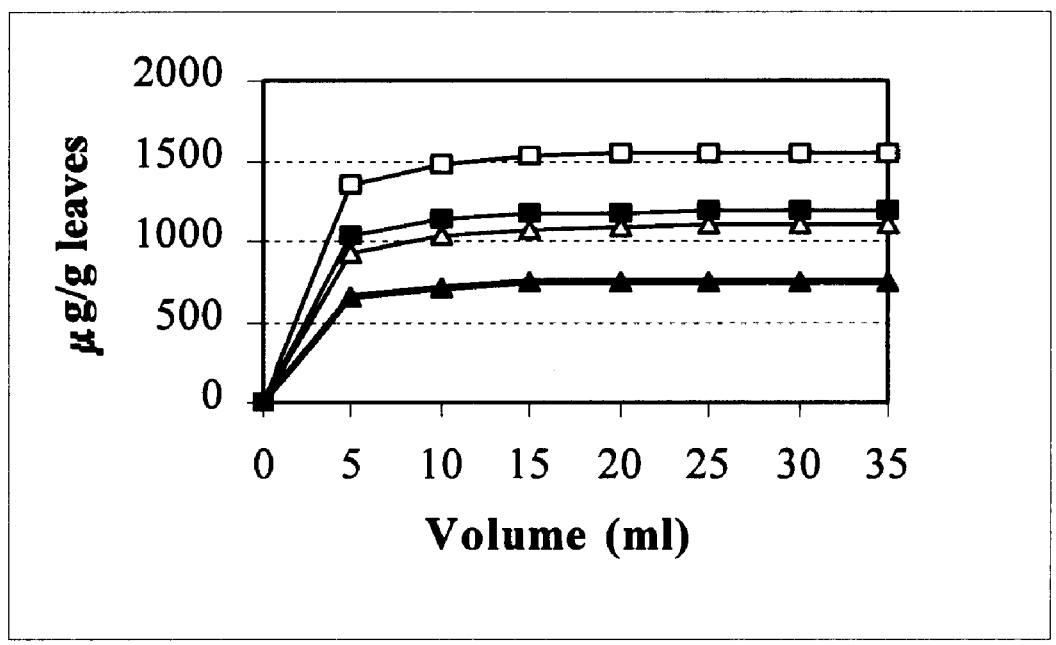
FIG. 7 is a graph of volume (mL) versus amount of material recovered (μg/g leaves extracted) which illustrates extraction yields versus extraction volumes for seven repetitions of static/dynamic extractions, with B-B (Δ), G-A (■), G-B (▲) and G-C (Δ)

Like supercritical fluid extraction (SFE), PWE can also be used for kinetic extraction studies. FIG. 7 shows the extraction curves of gingkolides and Bilobalide versus extraction volume. The volumes are not the cumulative volumes of a continuous extraction, but rather are the sum of separate and successive extractions.

FIG. 7 shows that the first 5 mL of extract removed 84–87% of the terpene trilactones, while more than 94% of the lactones were extracted in the first 10 mL. Because such a significant percentage of the terpene trilactones are extracted initially, prolonged extractions may be unnecessary or undesirable for economic reasons.

Using the same kinetic extraction, the efficiency of an extraction method can be estimated. Assuming that the total mass of a terpene trilactone originally in the ginkgo leaves is Mo, and the masses of this lactone extracted in the first, second and third extraction repetitions (or in the first, second and third 5 mL as in this case) are $M_1$, $M_2$, and $M_3$. The model of Walker et al. (*Analyst*, 119: 2789, 1994) developed for supercritical fluid extraction holds and the following equation applies:

$$Mo = M_1 + M_2^2/(M_2 - M_3)$$

Table 2 presents the calculated or predicted values of Mo for the terpene trilactones and the exhausted extraction results ($M_E$). The consistency between the predicted values and the experimental results suggests that the kinetic extraction model is applicable to PWE. This kinetic extraction model provides a method for analyzing extraction efficiency or to design optimum extraction procedures for maximum recovery in minimal extraction times.

TABLE 2

Predicted and Exhaustive Extraction Results for Terpene Trilactones

| Compounds | Predicted (µg/g leaves) | Extracted (µg/g leaves) | % of predicted |
|---|---|---|---|
| B-B | 1839 | 1857 | 101.0 |
| G-A | 1360 | 1355 | 99.6 |
| G-B | 771 | 783 | 101.6 |
| G-C | 1197 | 1227 | 102.5 |

Conclusions

Pressurized water extraction (PWE) at room temperature is a very effective and selective method for extracting terpene trilactones from Ginkgo leaves, especially for extracting thermally labile Bilobalide. Compared to conventional solvent boiling methods, PWE is a more time-, solvent- and energy-saving technique for the extractions of moderately polar to polar compounds from plant materials. By using the kinetic extraction model the efficiency of an extraction method can be estimated and therefore the extraction process can be tailored within the parameters of PWE as described herein for maximum yield with minimum time and cost.

As reported by others, the concentrations of gingkolides and Bilobalide in ginkgo leaves might vary significantly from tree to tree. However, it appears from the results that yellow Ginkgo leaves picked up in the late Fall contain no less of the terpene trilactones than the green leaves in summer or earlier times. Therefore, it should be ideal to collect yellow leaves instead of green leaves so that the Ginkgo tree is not harmed. For maximum recovery of the active lactone compounds, it is important to prevent leaves from molding during the sample drying and storage processes.

Example 2

Pressurized Water Extraction of Grape Seed

The PWE method is also effective for extracting polar and moderately polar compounds from plant seed material, for example, grape seed. One gram of grape seed powder (approximately 40 mesh, Montana Nutritional Laboratories, Lolo, Mont., from a plant of the genus Vitis) was placed on a bed of one gram of sea sand at the bottom of a 10-mL extraction cell. An ISCO 260D pump as described previously was used to control the pressure. The grape seed powder was exposed at room temperature and a pressure of 100 atm to four different extraction solvents [0.5%

NaH$_2$PO$_4$ in water (pH~5), pure water (pH~7), 0.5% Na$_2$HPO$_4$ in water (pH~8.5), and a mixture of water and ethanol (1:1)] for an initial ten to fifteen minutes of static extraction. Following the static extraction, a dynamic extraction at a flow rate of between about 1 mL/min and about 2 mL/min was performed until 20 mL of effluent was collected for each extraction solvent. The concentration of the extracted products was found to decrease with extraction volume, with the concentration of products appearing in the first 2 to 5 mL being the highest and falling to a minimum in the final few milliliters.

For comparison, samples of grape seed powder were also extracted, at room temperature and with sonication, using pure water or a mixture of water and ethanol for 15 minutes. The ratio of grape seed powder to extraction solvent was about 0.5 g to about 10 g per 100 mL of solvent. Thus, the sonication method required substantially more solvent than the PWE method to accomplish the extraction.

The yields of four moderately polar marker compounds extracted from grape seed using PWE and sonication extractions are summarized below in Table 3. These marker compounds are the phenolic compound gallic acid and three flavonoids, catechin, epicatechin, and epicatechin gallate. Catechin, epicatechin, epicatechin gallate and gallic acid have, respectively, structures V, VI, VII, and VIII above.

TABLE 3

Comparison of PWE and Sonication methods for extraction of Grape Seed Marker Compounds

| Method and Solvent | Yield of Gallic Acid[a] | Yield of Catechin[a] | Yield of Epicatechin[a] | Yield of Epicatechin Gallate[a] | Total of all Markers[a] |
|---|---|---|---|---|---|
| PWE pH 5 | 0.37 | 4.3 | 4.62 | 0.50 | 9.79 |
| PWE pH 7 | 0.64 | 7.10 | 7.61 | 0.83 | 16.18 |
| PWE pH 8.5 | 0.43 | 3.54 | 3.85 | 0.43 | 8.25 |
| PWE water/etoh (1:1) | 0.34 | 4.10 | 4.49 | 0.51 | 9.44 |
| Sonication Water | 0.57 | 6.85 | 7.34 | 0.83 | 15.5 |
| Sonication Ethanol | 0.54 | 6.66 | 7.28 | 0.82 | 15.3 |

[a]All yields expressed in μg/g grape seed powder.

The results shown in Table 3 above illustrate that an aqueous composition of pH=7 is most effective for PWE of gallic acid and flavonoids from grape seed. The results also illustrate that, at the proper pH, PWE can be more effective and efficient (only one-tenth the solvent needed for PWE as sonication) than the sonication method in removing these compounds from grape seed.

Having illustrated and described the principles of the invention in several embodiments, it should be apparent to those skilled in the art that the invention can be modified in arrangement and detail without departing from such principles. We claim all modifications coming within the spirit and scope of the following claims.

We claim:

1. A method for extracting material from a plant, comprising:
   providing a Ginkgo sample;
   exposing the sample to a liquid aqueous solvent at a temperature of from about 0° C. to about 100° C. and a pressure between about 50 atm and about 1000 atm; and
   isolating material solubilized in the liquid aqueous solvent.

2. The method of claim 1 where the sample is exposed to the liquid aqueous solvent by flowing the liquid aqueous solvent through the sample.

3. The method of claim 2 where the sample is pulverized and screened to a particle size of between about 20 mesh and about 80 mesh before exposure to the liquid aqueous solvent.

4. The method according to claim 3 where the particle size is from about 42 mesh to about 60 mesh.

5. The method of claim 3 where the pulverized and screened sample is mixed with a solid flow aid before exposure to the liquid aqueous solvent.

6. The method according to claim 5 where the flow aid is sand.

7. The method of claim 2 where exposing the sample to the liquid aqueous solvent is performed for less than about two hours.

8. The method according to claim 7 including a static extraction of about 20 minutes or less, followed by dynamic extraction.

9. The method of claim 1 where the Ginkgo sample comprises Ginkgo leaves.

10. The method of claim 9 where the temperature of the liquid aqueous solvent is between about 0° C. and about 80° C.

11. The method according to claim 9 where the temperature of the liquid aqueous solvent is between about 0° C. and about 60° C.

12. The method of claim 9 where the material includes terpene trilactones.

13. The method of claim 12 where the terpene trilactones include ginkgolides.

14. The method according to claim 13 where the terpene trilactone has the following formula:

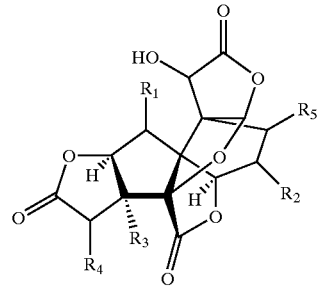

where R$_1$ is selected from the group consisting of —H and —OH; R$_2$ is selected from the group consisting of —H and —OH; R$_3$ is selected from the group consisting of —H and —OH; R$_4$ is selected from the group consisting of —H and lower aliphatic; and R$_5$ is selected from the group consisting of —H, —OH, and lower aliphatic.

15. The method according to claim 14 where R$_4$ is lower alkyl.

16. The method according to claim 14 where R$_4$ is methyl.

17. The method according to claim 14 where R$_5$ is lower alkyl.

18. The method according to claim 14 where R$_5$ is a sterically hinder lower alkyl.

19. The method according to claim 18 where R$_5$ is t-butyl.

20. The method according to claim 13 where the terpene trilactone has the formula

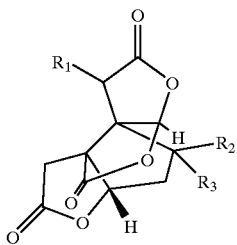

where $R_1$ is selected from the group consisting of H and —OH; and $R_2$ and $R_3$ are independently selected from the group consisting of —H, —OH, and lower aliphatic.

21. The method according to claim 20 where at least one of $R_2$ and $R_3$ is —OH.

22. The method according to claim 20 where at least one of $R_2$ and $R_3$ is lower alkyl.

23. The method according to claim 20 where at least one of $R_2$ and $R_3$ is t-butyl.

24. The method according to claim 13 where the terpene trilactone has the formula

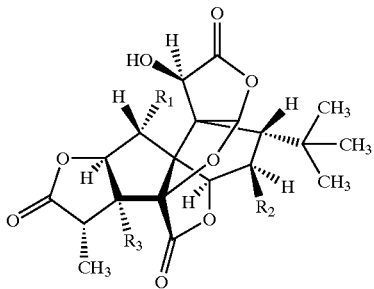

where $R_1$–$R_3$ are independently selected from the group consisting of —H and —OH.

25. The method according to claim 24 where $R_1=R_2=H$, and $R_3=OH$.

26. The method according to claim 24 where $R_1=R_3=OH$, and $R_2=H$.

27. The method according to claim 24 where $R_1=R_2=R_3=OH$.

28. The method according to claim 23 where the terpene trilactone is Bilobalide.

29. The method of claim 1 where the liquid aqueous solvent has a pH of from about 1 to about 7.

30. The method of claim 1 where the liquid aqueous solvent further comprises a modifier.

31. A method for extracting material from a plant of the genus Ginkgo, comprising:
providing a plant sample of the genus Ginkgo;
exposing the sample to a liquid aqueous solvent at a temperature from about 0° C. to about 100° C. and a pressure between about 50 atm and about 200 atm; and
isolating material solubilized in the liquid aqueous solvent.

32. The method of claim 31 where the sample is exposed to the liquid aqueous solvent by flowing the liquid aqueous solvent through the sample.

33. The method of claim 32 where the sample is pulverized and screened to a particle size of between about 20-mesh and about 80-mesh before exposing the sample to the liquid aqueous solvent.

34. The method according to claim 32 where the sample is pulverized and screened to a particle size of between about 42-mesh and about 60-mesh before exposing the sample to the liquid aqueous solvent.

35. The method of claim 33 where the pulverized and screened sample is mixed with sand before exposing the sample to the liquid aqueous solvent.

36. The method of claim 33 where exposing the sample to the liquid aqueous solvent continues for less than about one hour.

37. The method of claim 31 where the liquid aqueous solvent has a temperature between about 0° C. and about 60° C.

38. The method of claim 33 where the pH of the liquid aqueous solvent is less than about 7.

39. The method according to claim 33 where the material includes terpene trilactones.

40. The method according to claim 39 where the material includes ginkgolides.

41. The method according to claim 39 where the material includes bilobalides.

42. The method of claim 31 where the liquid aqueous solvent further comprises a modifier.

43. A method for extracting material from a plant, comprising:
providing a Ginkgo sample that has been milled and screened to a particle size in the range of 20 to 80 mesh;
exposing the sample to a liquid aqueous solvent at a temperature of from about 0° C. to about 100° C. and a pressure between about 50 atm and about 1000 atm; and
isolating material solubilized in the liquid aqueous solvent.

44. The method of claim 43 where exposing the sample to the liquid aqueous solvent composition comprises flowing the liquid aqueous solvent through the sample.

45. The method of claim 43 where the sample is mixed with sand after being milled and screened.

46. The method of claim 43 where exposing the sample to the liquid aqueous solvent continues for less than about one hour.

47. The method of claim 43 where the Ginkgo sample comprises Ginkgo leaves.

48. The method of claim 47 where the liquid aqueous solvent has a temperature of between about 0° C. and about 60° C.

49. The method of claim 47 where the material comprises terpene trilactones.

50. The method of claim 49 where the terpene trilactones are selected from the group consisting of Ginkgolides A–C, and mixtures thereof.

51. The method of claim 49 where the terpene trilactones comprise Bilobalide.

52. The method of claim 43 where the liquid aqueous solvent further comprises a modifier.

53. A method for isolating material from a plant, comprising:
exposing a Ginkgo sample to a liquid aqueous solvent having a temperature of from about 0° C. to about 60° C., a pH between about 2 and about 7 and a pressure between about 50 atm and about 200 atm for a static extraction period of less than about 20 minutes followed by a dynamic extraction, the sample having a mesh size of from about 42-mesh to about 60-mesh; and isolating material solubilized in the liquid aqueous solvent.

54. The method according to claim 53 where the sample is mixed with sand.

55. The method of claim 53 where the Ginkgo sample comprises Ginkgo leaves.

56. The method according to claim 53 where the material is a terpene trilactone having the formula

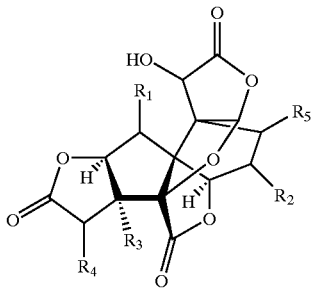

where $R_1$ is selected from the group consisting of —H and —OH; $R_2$ is selected from the group consisting of —H and —OH; $R_3$ is selected from the group consisting of —H and —OH; $R_4$ is selected from the group consisting of —H and lower aliphatic; and $R_5$ is selected from the group consisting of —H, —OH, and lower aliphatic.

57. The method according to claim 56 where $R_4$ is lower alkyl.

58. The method according to claim 57 where $R_4$ is methyl.

59. The method according to claim 56 where $R_5$ is lower alkyl.

60. The method according to claim 59 where $R_5$ is a sterically hindered lower alkyl.

61. The method according to claim 60 where $R_5$ is t-butyl.

62. The method according to claim 55 where the material is a terpene trilactone having a formula

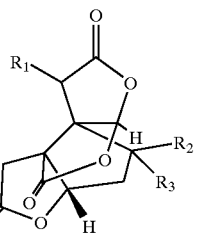

where $R_1$ is selected from the group consisting of H and —OH; and $R_2$ and $R_3$ are independently selected from the group consisting of —H, —OH, and lower aliphatic.

63. The method according to claim 62 where at least one of $R_2$ and $R_3$ is —OH.

64. The method according to claim 62 where at least one of $R_2$ and $R_3$ is lower alkyl.

65. The method according to claim 64 where at least one of $R_2$ and $R_3$ is t-butyl.

66. The method according to claim 53 where the material is a terpene trilactone having a formula

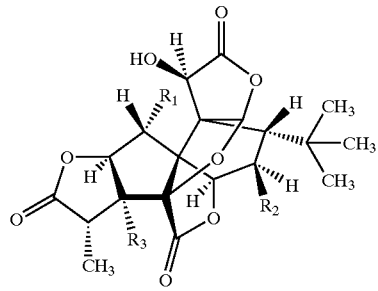

where $R_1$–$R_3$ are independently selected from the group consisting of —H, and —OH.

67. The method according to claim 66 where the material is selected from the group consisting of Ginkgolide A, B, C, and combinations thereof.

68. The method according to claim 64 where the material is bilobalide.

* * * * *